United States Patent [19]

Strike et al.

[11] 4,086,269

[45] Apr. 25, 1978

[54] 11-DEOXY-15-SUBSTITUTED PROSTAGLANDINS

[75] Inventors: Donald P. Strike, St. Davids; Wenling Kao, King of Prussia, both of Pa.

[73] Assignee: American Home Products Corporation, New York, N.Y.

[21] Appl. No.: 714,734

[22] Filed: Aug. 16, 1976

Related U.S. Application Data

[60] Division of Ser. No. 593,821, Jul. 7, 1975, Pat. No. 3,996,255, which is a continuation-in-part of Ser. No. 463,482, Apr. 24, 1974, abandoned.

[51] Int. Cl.² ............................................. C07C 177/00
[52] U.S. Cl. .................................. 260/514 D; 560/121
[58] Field of Search ........................ 260/468 D, 514 D

[56] References Cited

U.S. PATENT DOCUMENTS

| 3,816,393 | 6/1974 | Hayashi et al. ........................ 260/209 |
| 3,849,474 | 11/1974 | Abraham et al. ..................... 260/468 |

*Primary Examiner*—Robert Gerstl
*Attorney, Agent, or Firm*—Robert Wiser

[57] ABSTRACT

Processes for the total synthesis of dl-11-deoxy-15-substituted prostaglandins, novel intermediates therefore, certain novel final products, as well as optical resolutions of the final products are disclosed.

The final products are bronchodilators.

3 Claims, 2 Drawing Figures

11-DEOXY-15-SUBSTITUTED PROSTAGLANDINS

CROSS-REFERENCE TO CO-PENDING APPLICATION

This is a division of application Ser. No. 593,821 filed July 7, 1975 now U.S. Pat. No. 3,996,255, which is a continuation-in-part of application Ser. No. 463,482, filed Apr. 24, 1974, now abandoned.

BACKGROUND OF THE INVENTION

The synthesis of 11-deoxy-PGE$_2$ is described by Bagli and Bogri in Tetrahedron Letters, 1972, p. 3815. The octenol side chain in that synthesis is elaborated from a nitro methylene group introduced at the correct position on the cyclopropane ring by conjugate addition of nitro-methane. Synthesis of 11-desoxy PGE$_1$ using conjugate addition, to 2-(6'-carbo-alkoxyhexyl)-cyclopent-2-en-1-one of a vinyl copper reagent derived from tri-n-butyl-phosphine copper iodide and 1-lithio-3-(α-ethoxy)-ethoxy-oct-1-en is described in Netherlands patent 7301094 and by Sih et al. in Tetrahedron Letters, 1972, p. 2435. Netherlands Pat. No. 7301094 also suggests that methyl or ethyl are suitable alternative substituents in the 3-position of 1-lithio-3-(α-ethoxy)-ethoxy-oct-1-ene. Corey and Beames in the Journal of the American Chemical Society, 94, p. 7210, (1972) show the conjugate addition of a vinyl copper reagent derived from 1-pentynyl copper and 1-lithio-3-(dimethyl-5-butyl-silyloxy)-oct-1-en to cyclohex-2-en-3-one, and suggest the usefulness of this vinyl copper reagent in prostaglandin synthesis. 11-Deoxy-5 and 6-dehydro prostaglandins which are unsubstituted at the 15-position have also been prepared, but by processes different from those set forth in this application. These syntheses are reported in Canadian Journal of Chemistry, 49, 1070 (1971), Offenlegungsschrift 2, 313, 868 October 4, 1973, and Journal of Organic Chemistry, 39, 2506 (1974).

The present invention provides a direct method for the total synthesis of 11-deoxy-PGE type compounds substituted in the 15-position with such groups as ethynyl and methyl.

SUMMARY OF THE INVENTION

The invention sought to be patented in its first process aspect is described as residing in the concept of a process for the preparation of a compound of the formula:

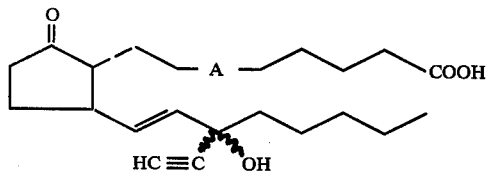

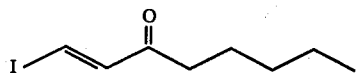

wherein A is a triple bond, a cis double bond, or a single bond which comprises:

a. treating a compound of the formula:

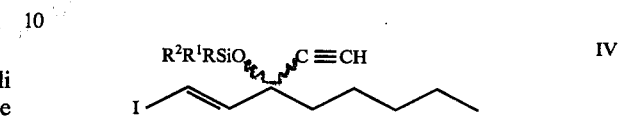

with an ethynyl Grignard reagent to produce a compound of the formula:

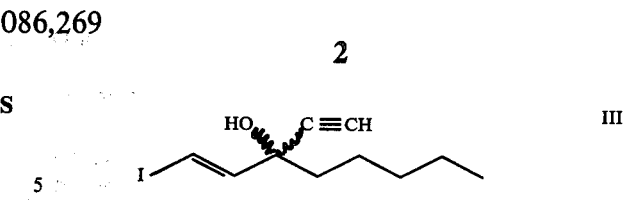

b. treating the product of step a with a tri(lower)alkyl silylating reagent to produce a compound of the formula:

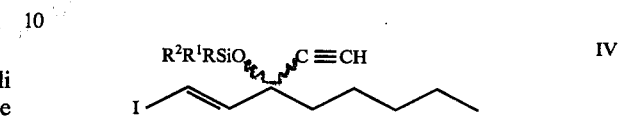

wherein R is lower alkyl of from 1 to 4 carbon atoms and R$^1$ and R$^2$ are independently selected from among the group consisting of straight chain lower alkyl of from 1 to 4 carbon atoms;

c. treating the product of step b with a Grignard reagent followed by treatment with a tri(lower)alkyl silylating reagent to produce a compound of the formula:

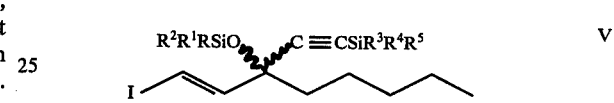

wherein R, R$^1$, and R$^2$ are as described hereinabove and R$^3$ is lower alkyl of from 1 to 4 carbon atoms, and R$^4$ and R$^5$ are independently selected from among the group consisting of straight chain lower alkyl of from 1 to 4 carbon atoms;

d. treating the product of step c with a lower alkyl lithium and then with a lower alkynyl copper;

e. treating the product of step d with a compound of the formula:

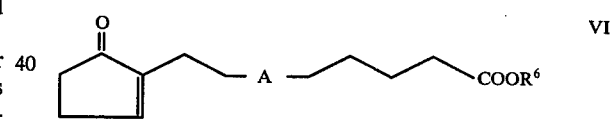

wherein A is as described hereinabove, and R$^6$ is lower alkyl to produce a compound of the formula:

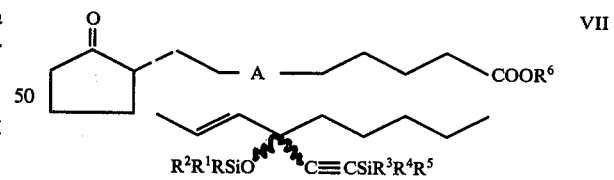

wherein A, R, R$^1$, R$^2$, R$^3$, R$^4$, R$^5$, and R$^6$ are as defined hereinabove;

f. contacting the product of step e with aqueous acid; and g. treating the product of step f with aqueous base.

The tangible embodiments produced by the first process aspect of the invention possess the inherent general physical properties of being oily liquids, being substantially insoluble in water and generally soluble in such common organic solvents as ethers, ketones, and esters, e.g. diethyl ether, acetone and ethyl acetate.

Examination of the products produced by the aforesaid process reveals upon infrared, ultraviolet, nuclear magnetic resonance, mass spectral, and thin layer chromatographic analysis, spectral data and migration rates supporting the molecular structure hereinbefore set forth.

The tangible embodiments produced by the first process aspect of the invention possess the inherent applied use characteristic of exerting bronchodilating effects in warm-blooded animals.

The invention sought to be patented in a second process aspect resides in the concept of a process for the preparation of a compound of the formula:

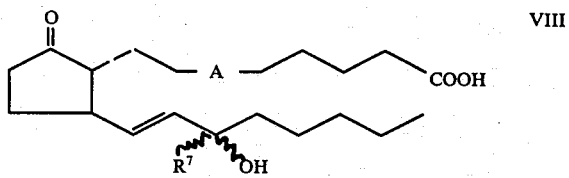
VIII wherein A is a triple bond and $R^7$ is a straight chain lower alkyl of from 1 to 3 carbon atoms; A is a cis double bond and $R^7$ is straight chain lower alkyl of from 1 to 3 carbon atoms, vinyl, or benzyl; or A is a single bond and $R^7$ is straight chain lower alkyl of from 1 to 3 carbon atoms, or vinyl which comprises:

a. treating a compound of the formula:

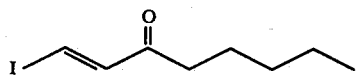
II with a lower alkyl, vinyl, or benzyl Grignard reagent to produce a compound of the formula:

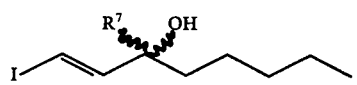
IX wherein $R^7$ is as defined hereinabove;

b. treating the product of step a with a tri(lower)alkyl silylating reagent to produce a product of the structure:

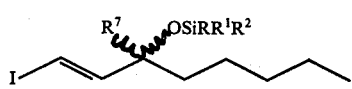
X wherein $R^7$ is as defined hereinabove; R is lower alkyl of from 1 to 4 carbon atoms, and $R^1$ and $R^2$ are independently selected from the group consisting of straight chain lower alkyl of from 1 to 4 carbon atoms;

c. treating the product of step b with a lower alkyl lithium and then with a lower alkynyl copper;

d. treating the product of step c with a compound of the formula:

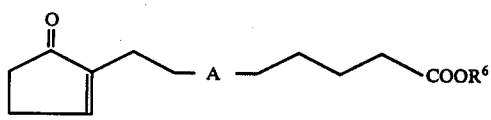
VI wherein A is as defined hereinabove, and $R^6$ is lower alkyl, to produce a compound of the formula:

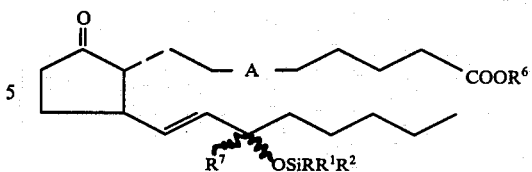
XI wherein A, R, $R^1$, $R^2$, $R^6$ and $R^7$ are as defined hereinabove;

e. contacting the product of step d with aqueous acid; and
f. contacting the product of step e with aqueous base.

The tangible embodiments produced by the second process aspect of the invention possess the inherent general physical properties of being oily liquids, being substantially insoluble in water, and generally soluble in such common organic solvents in ethers, ketones, and esters, such as diethyl ether, acetone and ethyl acetate.

Examination of the products produced by the aforesaid process reveals, upon infrared, ultraviolet, nuclear magnetic resonance, mass spectral, and thin layer chromatographic analysis, spectral data, and migration rates supporting the molecular structure hereinbefore set forth.

The tangible embodiments produced by the second process aspect of the invention possess the inherent applied use characteristic of exerting bronchodilating effects in warm-blooded animals.

The invention sought to be patented in its first composition aspect resides in the concept of a chemical compound which is 3-ethynyl-1-iodo-1-octen-3-ol.

The tangible embodiment of the first composition aspect of the invention possesses the inherent general physical properties of being a high boiling liquid, being substantially insoluble in water, and generally soluble in such common organic solvents as ethers, ketones, and esters, such as diethyl ether, acetone, and ethyl acetate.

Examination of the products produced by the aforedescribed process reveals, upon infrared, ultraviolet nuclear magnetic resonance, mass spectral and thin layer chromatographic analysis, spectral data and a migration rate supporting the molecular structure hereinbefore set forth.

The tangible embodiment of the first composition aspect of the invention possesses the inherent applied use characteristic of being an intermediate in the synthesis of compounds of Formula I.

The invention sought to be patented in its second composition aspect resides in the concept of a chemical compound having the formula:

wherein R is lower alkyl of from 1 to 4 carbon atoms; $R^1$ and $R^2$ are independently selected from among the group consisting of straight chain lower alkyl of from 1 to 4 carbon atoms; and X is —H or —$SiR^3R^4R^5$ wherein $R^3$ is lower alkyl of from 1 to 4 carbon atoms and $R^4$ and $R^5$ are independently selected from among the group consisting of straight chain lower alkyl of from 1 to 4 carbon atoms.

The tangible embodiments of the second composition aspect of the invention possess the inherent general physical properties of being oily liquids, and of being substantially soluble in such common organic solvents as tetrahydrofuran, and ether.

Examination of the products produced by the herein described process reveals upon infrared, ultraviolet, nuclear magnetic resonance, mass spectral and thin layer chromatographic analysis, spectral data, and migration rates supporting the molecular structure herein set forth.

The tangible embodiments of the second composition aspect of the invention possess the inherent applied use characteristic of being intermediates in the synthesis of compounds of Formula I.

The invention sought to be patented in its third composition aspect resides in the concept of a chemical compound having the formula:

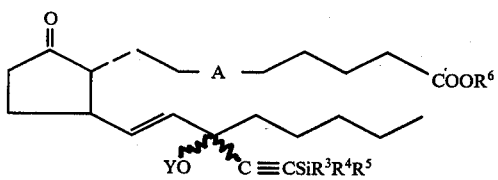

wherein A is a triple bond, a single bond, or a cis double bond; Y is H— or —SiRR$^1$R$^2$ wherein R is lower alkyl of from 1 to 4 carbon atoms, and R$^1$ and R$^2$ are independently selected from the group consisting of straight chain lower alkyl of from 1 to 4 carbon atoms; R$^3$ is lower alkyl; R$^4$ and R$^5$ are independently selected from among the group consisting of straight chain lower alkyl of from 1 to 4 carbon atoms; and R$^6$ is lower alkyl.

The tangible embodiments of the third composition aspect of the invention possess the inherent physical properties of being oily liquids, being substantially insoluble in water, and soluble in such common organic solvents as diethyl ether, ethyl acetate, and ethanol.

Examination of the products produced by the herein described process reveals, upon infrared, ultraviolet, nuclear magnetic resonance, mass spectral, and thin layer chromatographic analysis, spectral data and migration rates supporting the molecular structure hereinbefore set forth.

The tangible embodiments of the third composition aspect of the invention possess the inherent applied use characteristic of being intermediates in the synthesis of the compounds of Formula I.

The invention sought to be patented in a fourth process aspect resides in the concept of a process for the preparation of an optically active compound of the formula:

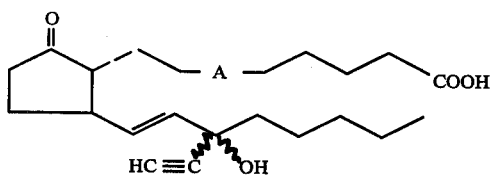

wherein A is a triple bond, a single, or a cis double bond; substantially free of its optical antipode which comprises:

a. treating a compound of the formula:

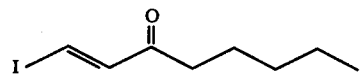

with an ethynyl Grignard reagent to produce a compound of the formula:

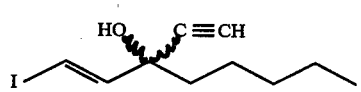

b. treating the product of step a with a tri(lower)alkyl silylating reagent to produce a compound of the formula:

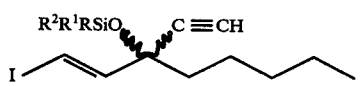

wherein R is lower alkyl of from 1 to 4 carbon atoms and R$^1$ and R$^2$ are independently selected from among the group consisting of straight chain lower alkyl of from 1 to 4 carbon atoms;

c. treating the produce of step b with a Grignard reagent followed by treatment with a tri(lower)alkyl silylating reagent to produce a compound of the formula:

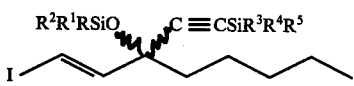

wherein R, R$^1$ and R$^2$ are as described hereinabove, and R$^3$ is lower alkyl of from 1 to 4 carbon atoms, and R$^4$ and R$^5$ are independently selected from among the group consisting of straight chain lower alkyl of from 1 to 4 carbon atoms;

d. treating the product of step c with a lower alkyl lithium and then with a lower alkynyl copper.

e. treating the product of step d with a compound of the formula:

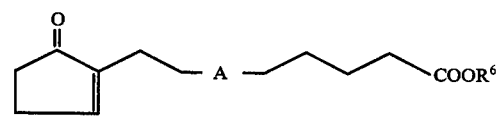

wherein A is as defined hereinabove; and R$^6$ is lower alkyl; to produce a compound of the formula:

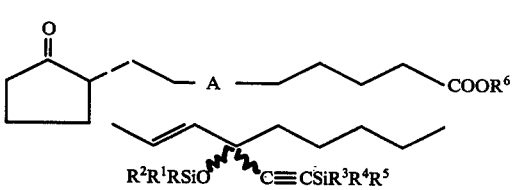

wherein A, R, R$^1$, R$^2$, R$^3$, R$^4$, R$^5$, and R$^6$ are as defined hereinabove;

f. contacting the product of step e above with aqueous acid;

g. contacting the product of step f above with aqueous base;

and h. treating the product of step g above with an optically active base; separating the enantiomeric salts so produced, and recovering the optically active acid from the separated salt.

The tangible embodiments produced by the fourth process aspect of the invention possess the inherent general physical properties of being oily liquids, being substantially insoluble in water, and generally soluble in such common organic solvents as ester, ketones, and ethers, e.g. diethyl ether, acetone, and ethyl acetate.

Examination of the products produced by the aforedescribed process reveals upon nuclear magnetic resonance, infrared, and polarimetric examination, spectral data and optical rotations supporting the molecular structure hereinbefore set forth.

The tangible embodiments produced by the fourth process aspect of the invention possess the inherent applied use characteristic of exerting bronchodilating effects in warm-blooded animals.

The invention sought to be patented in its fifth process aspect resides in the concept of a process for the production of an optically active compound of the formula:

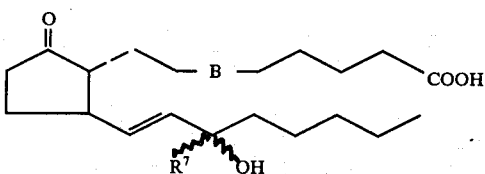
VIIIb wherein B is a triple bond and $R^7$ is lower alkyl of from 1 to 3 carbon atoms; or B is a single bond and $R^7$ is straight chain lower alkyl of from 1 to 3 carbon atoms, or vinyl; substantially free of its optical antipode, which comprises:

a. treating a compound of the formula:

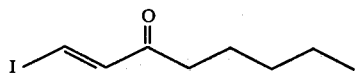
II with a lower alkyl, vinyl, or benzyl Grignard reagent to produce a compound of the formula:

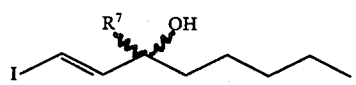
IX wherein $R^7$ is as defined hereinabove;

b. treating the product of step a above with a tri(lower-)alkyl silylating reagent to produce a product of the structure:

X wherein $R^7$ is as defined hereinabove; R is lower alkyl of from 1 to 4 carbon atoms; and $R^1$ and $R^2$ are independently selected from among the group consisting of straight chain lower alkyl of from 1 to 4 carbon atoms;

c. treating the product of step b with a lower alkyl lithium and then with a lower alkynyl copper;

d. treating the product of step c with a compound of the formula:

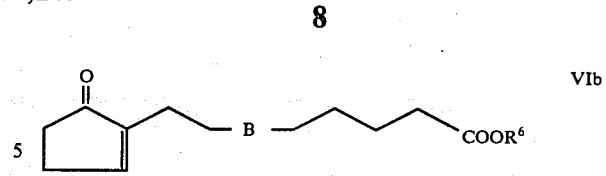
VIb wherein B is as defined hereinabove and $R^6$ is lower alkyl to produce a compound of the formula:

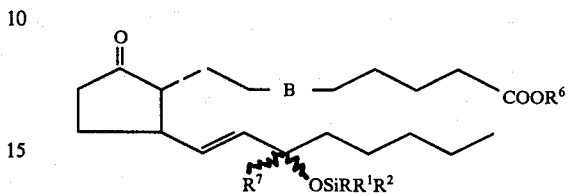

wherein B, R, $R^1$, $R^2$, $R^6$, and $R^7$ are as defined hereinabove;

e. contacting the product of step d with aqueous acid;
f. contacting the product of step e with aqueous base;
and g. treating the product of step f above with an optically active base; separating the enantiomeric salts so produced; and recovering the optically active acid from the separated salt.

The tangible embodiments produced by the fifth process aspect of the invention possess the inherent physical properties of being oily liquids, being substantially insoluble in water, and soluble in such common organic solvents as diethyl ether, ethyl acetate, and ethanol.

Examination of the products produced by the hereinabove described process reveals, upon infrared, ultraviolet, nuclear magnetic resonance, mass spectral, and thin layer chromatographic analysis spectral data and migration rates supporting the molecular structure hereinabove set forth.

The invention sought to be patented in its fourth composition aspect resides in the concept of a chemical compound of the formula:

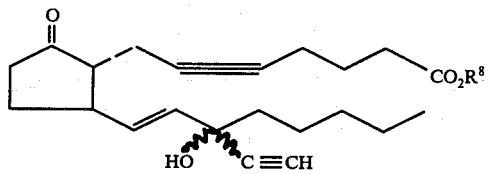

wherein $R^8$ is hydrogen, alkyl of from 1 to about 6 carbon atoms, alkali metal, or a pharmacologically acceptable cation derived from ammonia or a basic amine.

The tangible embodiments of the fourth composition aspect of the invention possess the inherent general physical properties of being clear to yellow oils, or crystalline solids, and when $R^8$ is hydrogen, are substantially insoluble in water and are generally soluble in organic solvents such as ethyl acetate and ether.

Examination of the compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, and the mode of synthesis, confirm the structure of the compositions sought to be patented.

The tangible embodiments of the fourth composition aspect of the invention possess the inherent applied use characteristic of exerting bronchodilating effects and reducing gastric secretion upon administration to warm-blooded animals as evidenced by pharmacological evaluation according to standard test procedures.

The invention sought to be patented in its fifth compositon aspect resides in the concept of a chemical compound of the formula:

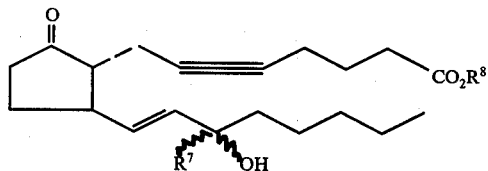

wherein $R^7$ is lower alkyl of from 1 to 3 carbon atoms; and $R^8$ is hydrogen, lower alkyl of from 1 to about 6 carbon atoms, alkali metal, or a pharmacologically acceptable cation derived from ammonia or a basic amine.

The tangible embodiments of the fifth composition aspect of the invention possess the inherent general physical properties of being clear to yellow oils, or crystalline solids, and when $R^8$ is hydrogen are substantially insoluble in water, and are generally soluble in organic solvents such as ethyl acetate and ether. Examination of the compounds produced according to the hereinafter described process reveals, upon infrared, nuclear magnetic resonance, and mass spectrographic analysis, spectral data supporting the structures herein set forth. The aforementioned physical characteristics taken together with the nature of the starting materials and the mode of synthesis further confirm the structure of the compositions sought to be patented.

The tangible embodiments of the fifth compositon aspect of the invention possess the inherent applied use characteristic of exerting bronchodilating effects upon administration to warm-blooded animals as evidenced by pharmacological evaluation according to standard test procedures.

The tangible embodiments of the products produced by the fifth process aspect of the invention possess the inherent applied use characteristics of exerting bronchodilating effects in warm-blooded animals.

DESCRIPTION OF THE PREFERRED EMBODIMENTS

In describing the processes of the invention reference will be made to the annexed drawings wherein.

Figure 1:
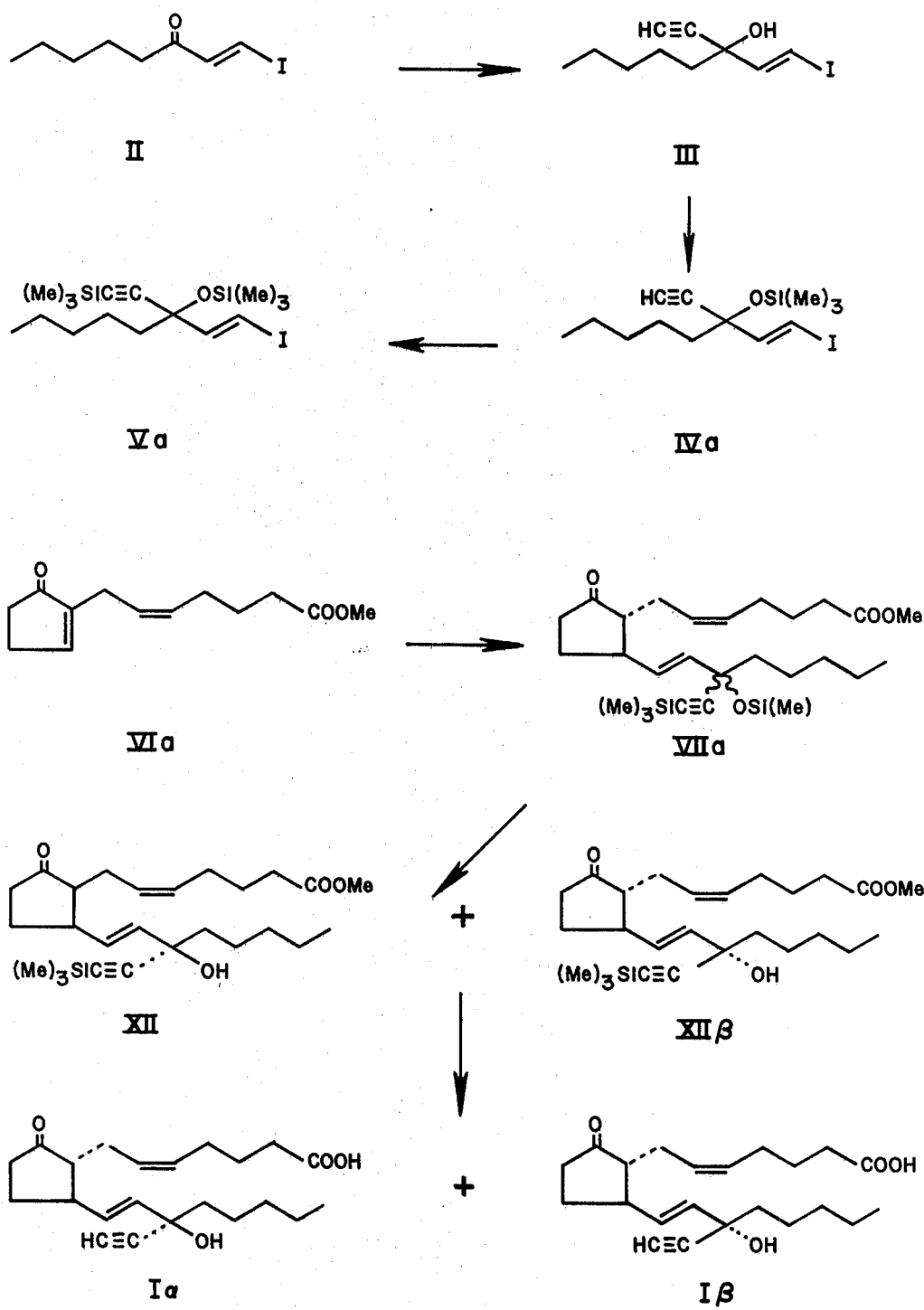
FIG. 1 illustrates schematically the process for the preparation of dl-7-(2β-[(3R)-3-ethynyl-3-hydroxy-trans-1-octenyl]-5-oxo-1α-cyclopentyl)-cis-5-heptenoic acid (Iα) and dl-7-(2β[(3S)-3-ethynyl-3-hydroxy-trans-1-octenyl]-5-oxo-1α-cyclopentyl)-cis-5-heptenoic acid (Iβ).

As shown in FIG. 1, 1-iodo-1-octen-3-ol (II) is treated with an ethynyl Grignard reagent, conveniently ethynyl magnesium bromide, in a suitable Grignard solvent of the ether type, conveniently tetrahydrofuran, at reduced temperature, conveniently 0° C., while stirring for a short time, conveniently 1 hour, to give dl-3-ethynyl-1-iodo-1-octen-3-ol (III).

If desired, III may be isolated by conventional means, for example distillation under high vacuum. Treatment of III with a mixture of hexamethyl disilazane, trimethylsilyl chloride and imidazole gives IVa. It will be obvious to a skilled organic chemist to substitute other well-known silylation reagents for the mixture of hexamethyl disilazane, trimethyl silyl chloride and imidazole to prepare the variously substituted silyloxy derivatives of formula IV. The reaction is normally performed in an inert solvent; tetrahydrofuran is convenient for this purpose. The time and temperature of the reaction are not critical and for convenience a 15 minute reaction period at room temperature is used. The isolation of IVa and the other compounds of formula IV may, if desired, be accomplished by standard techniques, for example, by chromatography on alumina. Treatment of IVa with a Grignard reagent, conveniently ethyl magnesium bromide and then with a trimethyl silylation reagent, conveniently, trimethyl silyl chloride, gives dl-1-iodo-3-trimethylsilylethynyl-3-trimethylsilyloxy-1-octene (Va). The substitution of other trialkyl silylation reagents for trimethylsilyl chloride will, of course, produce the other compounds of Formula V. The reaction is normally performed in an inert solvent, conveniently of an ether type, preferably tetrahydrofuran. The temperature of the reaction is also not especially critical, and for convenience the initial treatment with the Grignard reagent is commenced at 0° C. and allowed to finish at room temperature. For convenience, the silylation reaction is also performed at room temperature. Isolation of Va or the other compounds of Formula V may be accomplished by standard means; for example, distillation under high vacuum is especially convenient. If compound Va is treated with an alkyl lithium, conveniently t-butyl lithium, at reduced temperatures, conveniently −78°, then with an alkynyl copper, conveniently 1-pentynyl copper, which has been assisted in forming a solution by use of a complexing agent, conveniently hexamethyl phosphorous triamide, also at reduced temperature, conveniently −78° C., in an inert solvent, conveniently dry ether, and then treated, conveniently at the same temperature and in the same solvent system, with 7-(5-oxo-1-cyclopentenyl)-cis-5-heptenoic acid, methyl ester (VIa), di-7-(2β-[(3RS)-3-trimethyl silylethynyl-3-trimethyl silyloxy-trans-1-octenyl]-5-oxo-1α-cyclopentyl)-cis-5-heptenoic, methyl ester VIIa is produced. Similar treatment of other compounds of Formula V and Formula VI will produce the other compounds of Formula VII. If desired, compound VIIa and the other compounds of Formula VII may be isolated by conventional techniques, for example, chromatography on silica gel. Treatment of VIIa with aqueous acid, conveniently acetic acid containing some water, for convenience at room temperature, gives a mixture of dl-7-(2β-[(3-hydroxy-3-trimethylsilylethynyl-trans-1-octenyl]-5-oxo-1α-cyclopentyl)-cis-5-heptenoic acid, methyl ester (XIIα) and dl-7-(2β[(3S)-3-hydroxy-3-trimethylsilylethynyl-trans-1-octenyl]-5-oxo-1α-cyclopentyl)-cis-5-heptenoic acid, methyl ester (XIIβ). Similar treatment of other compounds of formula VII will give analogous compounds of Formula XII. If desired, the R and S isomers of Formula XII may be separated by conventional means, for example, chromatography on silica gel. If XIIα, XIIβ, or a mixture thereof is treated, at moderate temperature, conveniently room temperature, with aqueous base, conveniently sodium hydroxide in water, dl-7-(2β-[(3R)-3-ethynyl-3-hydroxy-trans-1-octenyl]-5-oxo-1α-cyclopentyl)-cis-5-heptenoic acid (Iα) and dl-7-(2β-[(3S)-3-ethynyl-3-hydroxy-trans-1-octenyl]-5-oxo-1α-cyclopentyl)-cis-5-heptenoic acid (Iβ), or a mixture thereof, respectively will be obtained.

Treatment of other compounds of Formula XII will give the corresponding compound of Formula I. If desired, Iα and Iβ may be isolated by conventional means, for example, by chromatography on silica gel.

Figure 2:
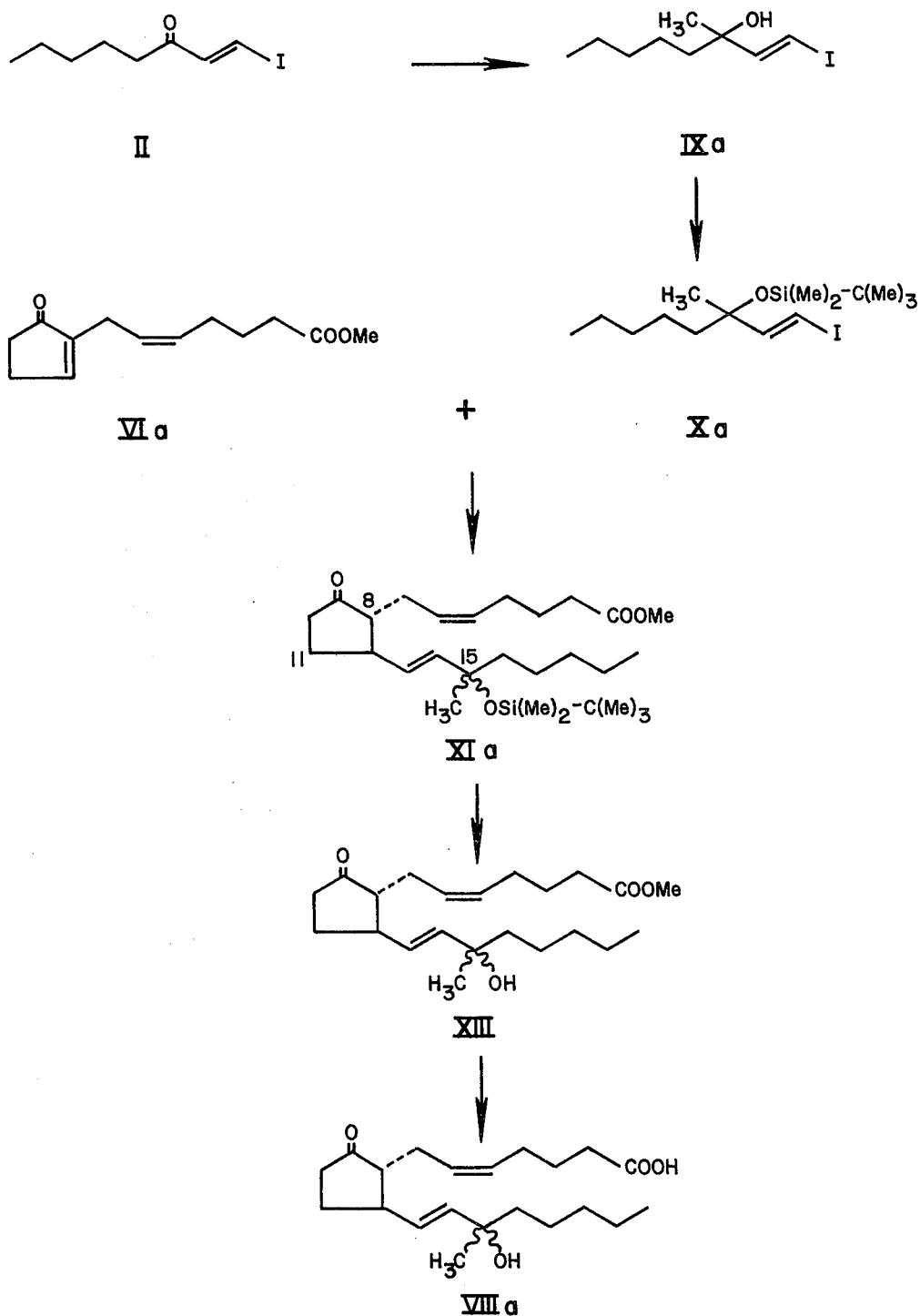
FIG. 2 illustrates schematically the process for the preparation of dl-7-(2β-[(3RS)-3-hydroxy-3-methyl-trans-octenyl]-5-oxo-1α-cyclopentyl)-cis-5-heptenoic acid (VIIIa).

As shown in FIG. 2, treatment of II with a methyl Grignard reagent conveniently methyl magnesium bromide, at reduced temperature, conveniently 0° C., in a suitable solvent of the ether type, conveniently diethylether, gives dl-1-iodo-3-methyl-1-octen-3-ol (IXa). Treatment of II with lower alkyl Grignard reagents under analogous conditions will produce the other compounds of Formula IX. If desired IXa and the other compounds of Formula IX may be isolated by standard means, for example, by chromatography on silica gel. Treatment of IXa with a mixture of imidazole and t-butyl dimethylsilyl chloride, in an inert solvent, conveniently dimethyl formamide, at moderately elevated temperature, conveniently 60° C., gives dl-1-iodo-3-t-butyldimethylsilyloxy-3-methyl-1-octene (Xa). Treatment of the other compounds of Formula IX with lower alkyl silylating agents under analogous conditions will give the other compounds of Formula X. If desired, Xa or the other compounds of Formula X may be isolated by standard means, for example, by chromatography on neutral alumina. Treatment of Xa with a lower alkyl lithium, conveniently t-butyl-lithium, followed by a 1-lower alkynyl copper conveniently 1-pentynyl copper, conveniently in the presence of a complexing agent, conveniently hexamethyl phosphorous triamide, in an inert solvent, conveniently diethyl ether, at reduced temperature, conveniently −78° C. followed by treatment with VIa in the same reaction system, initially at the temperature used for formation of the copper reagent, and then for a period at a higher temperature, conveniently 0° C. gives dl-7-(2β-[(3RS)-3-t-butyldimethylsilyloxy-3-methyl-trans-1-octenyl]-5-oxo-1α-cyclopentyl]-cis-5-heptenoic acid, methyl ester (XIa). Analogous treatment of the other compounds of Formula X will produce the other compounds of Formula XI. If desired, XIa or the other compounds of Formula XI may be isolated by standard means. For example, chromatography on silica gel is convenient. Treatment of XIa at moderate temperature, conveniently room temperature, in aqueous acid gives dl-7-(2β-[(3RS)-3-hydroxy-3-methyl-trans-1-octenyl]-5-oxo-1α-cyclopentyl)-cis-5-heptenoic acid, methyl ester (XIII). Analogous treatment of the other compounds XI will also give esters similar to XIII, having the free hydroxyl group on the octenyl side chain. If desired, XIII, or esters of similar structure may be isolated by standard means, for example, by chromatography on silica gel. Treatment of XIII, or of the related esters, at moderate temperatures, conveniently room temperature, with dilute alkali, conveniently 0.1 N aqueous sodium hydroxide mixed with an equal portion of tetrahydrofuran, gives Dl-7-(2β-[(3RS)-3-hydroxy-3-methyl-trans-1-octenyl]-5-oxo-1α-cyclopentyl)-cis-5-heptenoic acid (VIIIa). Analogous treatment of other compounds XIII will give analogous compounds of Formula VIII. If desired, VIII may be isolated by standard means, for example by chromatography on silica gel.

The substitution of other Grignard reagents, such as ethyl, propyl, vinyl, or benzyl Grignard reagent, for the methyl Grignard reagent described will be obvious to those skilled in the art.

The starting materials for the practice of the invention, namely 1-iodo-1-octene-3-one (II), 7-( 5-oxo-1-cyclopentenyl)-cis-5-heptenoic acid, lower alkyl esters, 7-(5-oxo-1-cyclopentenyl)heptanoic acid, lower alkyl esters, and 7-(5-oxo-1-cyclopentenyl)- 5-heptynoic acid, lower alkyl esters are known in the literature. II is described by Corey and Beames in the Journal of the American Chemical Society, 94, 7210, (1972). 7-(5-Oxo-1-cyclopentenyl)-cis-5-heptenoic acid methyl ester may be prepared as described in Tetrahedron Letters, 1972, p. 3815 and other lower alkyl esters of this acid may be prepared in an analogous fashion. 7-(5-Oxo-1-cyclopentenyl)-heptanoic acid lower alkyl esters may be prepared from 7-(5-oxo-1-cyclopentenyl)-cis-5-heptenoic acid lower alkyl esters by the procedure of Example 13, or they may be obtained as described by Bagli and Borgri in the Journal of Organic Chemistry, 37, p. 2132, (1972). 7-(5-Oxo-1-cyclopentenyl)-5-heptynoic acid lower alkyl esters may be prepared by the method described in Tetrahedron Letters, 1972, p. 3815.

It will be apparent to those skilled in the art that the carbon atoms in the octane side chain, or its precursors to which hydroxylic or protected hydroxylic substituents are attached are assymetric carbon atoms, and as a consequence these positions can be either of two epimeric configurations. The symbol   where used in this specification is to indicate that both possible configurations at each particular position is intended and is included within the scope of the invention.

Those skilled in the art will similarly recognize that reaction of the alkynyl copper reagent derived from compound V or X with compound VI will occur in a fashion wherein the side chains of the product will be substantially all trans oriented at their junction with the ring and that as usual a dl pair will be formed. The resolution of the dl pair into its optically active enantiomers may e accomplished by standard means. Salt formation with optically active bases such as quinine, strychnine, or brucine is a convenient method. For convenience in schematic representation only the natural configuration has been used to depict the dl pair, as well as the resolved enantiomers.

The esters of the fourth and fifth composition aspects ($R^8$ is alkyl) are prepared by standard methods, such as for example, by treating a solution of the free acids with diazomethane or other appropriate diazohydrocarbons, such as diazoethane, 1-diazo-2-ethylpentane, and the like. The alkali metal carboxylates of these aspects of the invention can be prepared by mixing stoichiometrically equivalent amounts of the free acids of formula I, preferably in aqueous solution, with solutions of alkali metal bases, such as sodium, potassium, and lithium hydroxides or carbonates, and the like, then freeze drying the mixture to leave the product as a residue. The amine salts can be prepared by mixing the free acids, preferably in solution, with a solution of the appropriate amine, in water, isopropanol, or the like, and freeze drying the mixture to leave the product as a residue.

The term "lower alkyl" when used herein and in the appended claims, unless specifically limited by the context, includes straight and branched chain hydrocarbon radicals, having from 1 to 6 carbon atoms, among which are included, for the sake of illustration but without limiting the generality thereof, methyl, ethyl, i-propyl, t-butyl, and the like.

The term "tri(lower)alkyl silylating reagents" when used herein and in the appended claims, means those substances or mixtures of substances, which are known to those skilled in organic chemistry, to replace the active hydrogen in a hydroxyl group or the —Mg halide moiety from a Grignard reagent with a tri(lower)alkyl silyl group. Among these are, for the purpose of illustration, but without limiting the generality of the foregoing, imidazole and t-butyldimethylsilylchloride; hexamethyldisilazane, trimethylsilylchloride and imidazole; and trimethylsilylchloride.

"Alkali metal" includes, for example, sodium, potassium, lithium, and the like. A "pharmacologically-acceptable cation derived from ammonia or a basic amine" contemplates the positively charged ammonium ion and analogous ions derived from organic nitrogenous bases strong enough to form such cations. Bases useful for the purpose of forming pharmacologically-acceptable non-toxic addition salts of such compounds containing free carboxyl groups form a class whose limits are readily understood by those skilled in the art. Merely for illustration, they can be said to comprise, in cationic form, those of the formula:

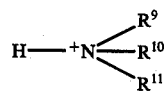

wherein $R^9$, $R^{10}$, and $R^{11}$, independently, are hydrogen, alkyl of from about 1 to about 6 carbon atoms, cycloalkyl of from about 3 to about 6 carbon atoms, monocarbocyclicaryl of about 6 carbon atoms, monocarbocyclicarylalkyl of from about 7 to about 11 carbon atoms, hydroxyalkyl of from about 1 to about 3 carbon atoms, or monocarbocyclicarylhydroxyalkyl of from about 7 to about 15 carbon atoms, or, when taken together with the nitrogen atom to which they are attached, any two of $R^9$, $R^{10}$, and $R^{11}$ form part of a 5 to 6-membered heterocyclic ring containing carbon, hydrogen, oxygen, or nitrogen, said heterocyclic rings and said monocarbocyclicaryl groups being unsubstituted or mono- or dialkyl substituted, said alkyl groups containing from about 1 to about 6 carbon atoms. Illustrative therefore of R groups comprising pharmacologically-acceptable cations derived from ammonia or a basic amine are ammonium, mono- di-, and trimethylammonium, mono-, di- and triethylammonium, mono-, di-, and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl-piperidinium, 2-methylpiperidinium, 1-ethyl-2-methylpiperidinium, mono-, di- and triethanolammonium, ethylidiethanolammonium, n-butylmonoethanolammonium, tris(hydroxymethyl)-methylammonium, phenylmonoethanolammonium, and the like.

In using the compositions produced by the instant invention they can be administered in a variety of dosage forms, the oral route being used primarily for maintenance therapy while injectables tend to be more useful in acute emergency situations. Inhalation (aerosols and solution for nebulizers) seems to be somewhat faster acting than other oral forms but slower than injectables and this method combines the advantages of maintenance and moderately-acute stage therapy in one dosage unit.

The daily dose requirements vary with the particular compositions being employed, the severity of the symptoms being presented, and the animal being treated. The dosage varies with the size of the animal. With large animals (about 70 kg. body weight), by the oral inhalation route, with for example a hand nebulizer or a pressurized aerosol dispenser the dose is from about 5 micrograms to about 100 micrograms, and preferably from about 10 to about 50 micrograms, approximately every four hours, or as needed. By theoral ingestion route, the effective dose is from about 1 to about 20 mg., preferably from about 5 to about 15 mg. up to a total of about 40 mg per day. By the intravenous route, the ordinarily effective dose is from about 50 micrograms to about 300 micrograms, preferably about 200 micrograms per day.

For unit dosages, the active ingredient can be compounded into any of the usual oral dosage forms including tablets, capsules and liquid preparations such as elixirs and suspensions containing various coloring, flavoring, stabilizing and flavor masking substances. For compounding oral dosage forms the active ingredient can be diluted with various tableting materials such as starches of various types, calcium carbonate, lactose, sucrose and dicalcium phosphate to simplify the tableting and capsulating process. A minor proportion of magnesium stearate is useful as a lubricant. In all cases, of course, the proportion of the active ingredient in said composition will be sufficient to impart bronchodilating activity thereto. This will range upward from about 0.0001% by weight of active ingredient in said composition.

For administration by the oral inhalation route with conventional nebulizers or by oxygen aerosolization it is convenient to provide the instant active ingredient in dilute aqueous solution, preferably at concentrations of about 1 part of medicament to from about 100 to 200 parts by weight of total solution. Entirely conventional additives may be employed to stabilize these solutions or to provide isotonic media, for example, sodium chloride, sodium citrate, citric acid, sodium bisulfite, and the like can be employed.

For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizers. Instead of a co-solvent there can also be used a dispersing agent such as oleyl alcohol. Suitable means to employ the aerosol inhalation therapy technique are described fully in U.S. Pat. Nos. 2,868,691 and 3,095,355, for example.

The following examples further illustrate the best mode contemplated by the inventors for carrying out the processes of their invention.

EXAMPLE 1 dl-3-Ethynyl-1-Iodo-1-Octen-3-01

A solution of 7.9 g. of 1-iodo-1-octen-3-one in 30 ml. of tetrahydrofuran is added dropwise over 10 minutes to an ice-cooled solution of ethynyl magnesium bromide (prepared from 21 ml. of 3M methyl magnesium bromide in ether and excess acetylene) in 170 ml. of tetrahydrofuran. After stirring at 0° for 1 hour under nitrogen, the mixture is added to ammonium chloride solution and extracted with ether. The extract is washed, dried, evaporated and the residue distilled to obtain the title product, 5.05 g., b.p. 55°–65°/.005 mm.

I. R. Analysis: $\lambda_{max}^{film}$ 3.0, 3.4, 4.75(w), 6.2, 9.8, 10.6μ.

NMR Analysis: Signal at δ=0.90 (triplet, 3 proton, terminal (CH$_3$), 2.62 (singlet, 1 proton, OH), 2.70 (singlet, 1 proton, —C≡CH), 6.65 (multiplet, 2 proton, olefinic) ppm.

Mass Spectral Analysis: Calc. M$^+$-17 261 m/e: Found M$^+$-17 261 m/e.

EXAMPLE 2 dl-3-Ethynyl-1-Iodo-3-Trimethylsilyloxy-1-Octene

A solution of 2.78 g. of dl-3-ethynyl-1-iodo-1-octen-3-ol in 15 ml. of tetrahydrofuran is treated at 0° C. with 6 ml. of hexamethyldisilazane, 0.5 ml. of trimethylsilylchloride and 1.0 g. of imidazole. The mixture is stirred at 25° C. for 15 minutes and then evaporated with a water pump. The residue is extracted with n-hexane and the extract passed through alumina to afford the title product as an oil, 3.50 g.

I. R. Analysis: $\lambda_{max}^{film}$ 3.05, 3.4, 6.8, 8.0, 9.1, 10.55, 11.3, 11.85, 13.20 μ.

NMR Analysis: Signals at δ 0.17 (singlet, 9 proton, Si—CH$_3$), 0.90 (triplet, 3 proton, C—CH$_3$), 2.63 (singlet, 1 proton, C≡CH), 6.53 (singlet, 2 proton, olefinic H) ppm.

Mass Spectral Analysis: Calc. M$^+$ —CH$_{33}$ 335 m/e: Found M$^+$ —CH$_3$ 335 m/e.

EXAMPLE 3 dl-1-Iodo-3-Trimethylsilylethynyl-3-Trimethylsilyloxy-1-Octene

A solution of 3.3 g. of dl-3-ethynyl-1-iodo-3-trimethylsilyloxy-1-octene in 10 ml. of THF is treated at 0° C. under N$_2$ with 3 ml. of 3M ethyl magnesium bromide and stirred at 25° C. for ½ hour. The mixture is then treated at 0° C. with 3.5 ml. of trimethylchlorosilane and stirred at 25° C. for an additional 2½ hours. The whole mixture is added to aqueous ammonium chloride solution and extracted with ether. After washing with brine and drying over magnesium sulfate, the extract is evaporated. Distillation of the residue gives the title product, as an oil, 2.5 g. b.p. 79°–81° C. (0.025 mm).

I. R. Analysis: $\lambda_{max}^{film}$ 3.4, 4.6, 6.2, 8.0, 9.1, 10.58, 11.85, 13.14 μ.

NMR Analysis: Signals at δ 0.18 (singlet, 18 proton, Si—CH$_3$), 0.89 (triplet, 3 proton, C—CH$_3$), 6.46 (singlet, 2 proton, olefinic H) ppm.

Mass Spectral Analysis: Calc. M$^+$ —CH$_3$ 407 m/e: Found M$^+$ —CH$_3$ 407 m/e.

EXAMPLE 4 dl-7-(2β-[(3RS)-3-Trimethylsilylethynyl-3-Trimethylsilyloxy-Trans-1-Octenyl]-5-Oxo-1α-Cyclopentyl)-Cis-5-Heptenoic Acid, Methyl Ester A solution of 2.1 g. of dl-1-iodo-3-trimethylsilylethynyl-3-trimethyl-silyloxy-1-octene in 15 ml. of dry ether is treated at —78° C. under N$_2$ with 8.4 ml. of 1.2 M tert.-butyl lithium and stirred at —78° C. for 2 hours.

A suspension of 0.65 g. of 1-pentynyl copper in 10 ml. of dry ether is treated at 25° C. under N$_2$, with 1.63 g. of hexamethylphosphorus triamide and stirred at 25° C. for ½ hour.

The two above mixtures are combined at —78° C. by addition of the second one to the first one. The resulting solution is treated at —78° C. with 1.0 g. of 7-(5-oxo-1-cyclopentenyl)-cis-5-heptenoic acid, methyl ester in 3 ml. of dry ether. After stirring at —78° C. for ½ hour and at 0° C. for one hour, the mixture is added to aqueous ammonium sulfate solution and extracted with ether. The extract is washed with ice-cold 2% aqueous sulfuric acid solution, with brine and dried with magnesium sulfate. The solvent is evaporated and the residue chromatographed on silica gel. Elution with 6% ethyl acetate in hexanes gives the title product as an oil, 0.69 g.

I. R. Analysis: $\lambda_{max}^{film}$ 3.40, 4.60, 5.70, 6.95, 8.0, 8.65, 9.55, 10.3, 11.88, 13.15 μ.

NMR Analysis: Signals at δ 0.18 (singlet, 18 proton, Si—CH$_3$), 0.9 (triplet, 3 proton, C—CH$_3$), 3.66 (singlet, 3 proton, COOCH$_3$), 5.39 (multiplet, 2 proton, 5 & 6-H), 5 63 (multiplet, 2 proton, 13 & 14-H) ppm.

Mass Spectral Analysis: Calc. M$^+$ 518 m/e: Found M$^+$ 518 m/e.

EXAMPLE 5 dl-7-(2β-[(3R)-3-Hydroxy-3-Trimethylsilylethynyl-Trans-1-Octenyl]-5-Oxo-1α-Cyclopentyl)-Cis-5-Heptenoic Acid, Methyl Ester and dl-7-(2β-[(3S)-3-Hydroxy-3-Trimethylsilylethynyl-Trans-1-Octenyl]-5-Oxo-1α-Cyclopentyl)-Cis-5-Heptenoic Acid, Methyl Ester A solution of 0.54 g. of dl-7-(2β-[(3RS)-3-trimethylsilylethynyl-3-trimethylsilyloxy-trans-1-octenyl]-5-oxo-1α-cyclopentyl)-cis-5-heptenoic acid, methyl ester in 3 ml. of acetic acid and 1 ml. of water is stirred at 25° C. under N$_2$ for 3/4 hours. The solvent is evaporated at 25° C. in vacuo and the residue chromatographed on silica gel. Elution with 6% ethyl acetate in hexanes gives the first title product as an oil, 0.15 g.

I.R. Analysis: $\lambda_{max}^{film}$ 2.9, 3.4, 4.55, 5.7, 6.9, 7.98, 8.6, 9.8, 10.25, 11.5, 11.8, 13.1, 14.25 μ.

NMR Analysis: Signals at δ 0.18 (singlet, 9 protons, Si—CH$_3$), 0.90 (triplet, 3 protons, C—CH$_3$), 3.68 (singlet, 3 protons, COOCH$_3$), 5.43 (multiplet, 2 protons, 5 & 6-H), 5.71 (multiplet, 2 protons, 13 & 14-H) ppm.

Mass Spectral Analysis: Calc. M$^+$ 446 m/e: Found M$^+$ 446 m/e.

Continuing elution with 6% ethyl acetate in hexanes gives the second title product as an oil, 0.12 g.

I. R. Analysis: $\lambda_{max}^{film}$ 2.9, 3.4, 4.6, 5.7, 6.93, 8.0, 8.15, 9.8, 10.27, 11.55, 11.85, 13.14, 14.30 μ.

NMR Analysis: Signals at δ 0.18 (singlet, 9 protons, Si—CH$_3$), 0.9 (triplet, 3 protons, C—CH$_3$), 3.67 (singlet, 3 protons, COOCH$_3$), 5.43 (multiplet, 2 protons, 5 & 6-H), 5.72 (multiplet, 2 protons, 13 & 14-H) ppm.

Mass Spectral Analysis: Calc. M$^+$ 446 m/e: Found M$^+$ 446 m/e.

dl-7-(2β-[(3R)-3-Ethynyl-3-Hydroxy-Trans-1-Octenyl)]-5-Oxo-1α-Cyclopentyl)-Cis-5-Heptenoic Acid and dl-7-(2β-[(3S)-3-Ethynyl-3-Hydroxy-Trans-1-Octenyl)]-5-Oxo-1α-Cyclopentyl)-Cis-5-Heptenoic Acid A 0.5 g. mixture of dl-7-(2β-[(3R)-3-hydroxy-3-trimethylsilylethynyl-trans-1-octenyl]-5-oxo-1α-cyclopentyl)-cis-5-heptenoic acid, methyl ester and dl-7-(2β-[(3S)-3-hydroxy-3-trimethylsilylethynyl-trans-1-octenyl]-5-oxo-1α-cyclopentyl)-cis-5-heptenoic acid, methyl ester in 10 ml. of THF is treated at 25° C. under N$_2$ with 10 ml. of 1M sodium hydroxide solution. The solution is stirred at 25° C. for 24 hours and then acidified with acetic acid. The mixture is diluted with ether, washed with brine and dried with magnesium sulfate.

The solvent is evaporated and the residue chromatographed on silica gel. Elution with 20% ethyl acetate in hexanes gives the first title product as an oil, 0.05 g.

I. R. Analysis: $\lambda_{max}^{film}$ 3.05, 3.4, 5.8, 6.8, 7.1, 8.65, 9.85, 10.3 $\mu$.

NMR Analysis: Signals at $\delta$ 0.9 (triplet, 3 protons, CH$_3$), 2.58 (singlet, 1 proton, C≡CH), 5.54 (multiplet, 2 protons, 5 & 6-H), 5.58 (singlet, 2 protons, OH), 5.90 (multiplet, 2 protons, 13 & 14-H) ppm.

Mass Spectral Analysis: Calc. M$^+$-H$_2$O 342 m/e: Found M$^+$-H$_2$O 342 m/e.

Continuing elution with 20% ethyl acetate in hexanes gives the second title product as an oil, 0.05 g.

I. R. Analysis: $\lambda_{max}^{film}$ 3.05, 3.4, 5.85, 6.8, 7.05, 8.6, 9.8, 10.28 $\mu$.

NMR Analysis: Signals at $\delta$ 0.9 (triplet, 3 protons, CH$_3$), 2.59 (singlet, 1 proton, C≡CH), 5.42 (quintuplet, 2 protons, 5 & 6-H), 5.70 (singlet, 2 protons, OH), 5.90 (multiplet, 2 protons, 13 & 14-H) ppm.

Mass Spectral Analysis: Calc. M$^+$ 360 m/e: Found M$^+$ 360 m/e.

EXAMPLE 7 dl-1-Iodo-3-Methyl-1-Octen-3-Ol

An ice-cooled solution of 7.2 g. of 1-iodo-1-octen-3-one in 100 ml. of tetrahydrofuran is treated with 25 ml. of 3M methyl magnesium bromide in ether over 10 minutes under nitrogen. After stirring at 0° for 1 hour, the reaction mixture is added to saturated ammonium chloride solution, acidified with acetic acid and extracted with ether. After washing and drying, the ether extract is evaporated and the residue chromatographed on silica. Elution with 20% ethyl acetate in hexane gives the title product as an oil, 4.8 g.

I. R. Analysis: $\lambda_{max}^{film}$ 2.95, 3.4, 6.2, 6.8, 7.25, 8.4, 10.5 $\mu$.

NMR Analysis: Signals at $\delta$ 0.90 (triplet, 3 protons, terminal CH$_3$), 1.28 (singlet, C-3 methyl), 1.62 (singlet, OH), 6.35 and 6.72(doublet, 1 proton, J=15, olefinic) ppm.

Mass Spectral Analysis: Calc. M$^+$-17 251 m/e: Found M$^+$-17 251 m/e. Calc. M$^+$-71 197 m/e: Found M$^+$-71 197 m/e.

EXAMPLE 8 dl-1-Iodo-3-t-Butyldimethylsiloxy-3-Methyl-1-Octene

A solution of 2.625 g. of dl-1-iodo-3-methyl-1-octen-3-ol, 3.2 g. of imidazole and 3.6 g. of t-butyldimethylsilyl chloride in 10 ml. of dimethyformamide is stirred at 60° C. for 35 hours under nitrogen. After vacuum evaporation of the solvent, the residue is extracted with hexane and chromatographed on neutral alumina (Activity 3). Elution with hexane gives the title product as an oil, 2.5 g.

I. R. Analysis: $\lambda_{max}^{film}$ 3.45, 6.2, 6.85, 8.0, 9.95, 12.0, 12.95 $\mu$.

NMR Analysis: Signals at $\delta$ 0.08 (singlet, Si(CH$_3$)$_2$), 0.90 (singlet, t-butyl), 1.28 (singlet, C-3 methyl), 6.22 and 6.62 (doublet, J=15, olefinic) ppm.

Mass Spectral Analysis: Calc. M$^+$ + 1 383 m/e: Found M$^+$ + 1 383 m/e.

Analysis For: C$_{15}$H$_{31}$OISi: Calculated: I, 33.19; Found: I, 33.44.

EXAMPLE 9 dl-7-(2$\beta$-[(3RS)-3-t-Butyldimethylsilyloxy-3-Methyl-Trans-1-Octenyl]-5-Oxo-1$\alpha$-Cyclopentyl)-Cis-5-Heptenoic Acid, Methyl Ester A solution of 1.95 g. of dl-1-iodo-3-t-butyldimethylsilyloxy-3-methyl-1-octene in 20 ml. of ether under nitrogen is cooled in a dry ice-acetone bath and treated with 8.1 ml. of 1.24 M t-butyl lithium in pentane. After stirring at −78° for 2 hours, a freshly prepared solution of 1.65 g. of hexamethyl-phosphorous triamide and 0.655 g. of n-propylethynyl copper in 20 ml. of ether is added to the reaction mixture and stirring continued for 0.5 hours under nitrogen at −78°. A solution of 1.01 g. of 7-(5-oxo-1-cyclopentyl)-cis-5-heptenoic acid, methyl ester in 10 ml. of ether is then added and the mixture stirred at −78° for 0.5 hours and at 0° C. for 0.5 hours. The reaction mixture is added to saturated ammonium chloride solution, extracted with ether and the extract washed with 2% sulfuric acid, filtered through Celite, washed with dilute sodium bicarbonate, water and dried. Evaporation and silica chromatography of the residue give the title product as an oil, 1.063 g.

I. R. Analysis: $\lambda_{max}^{film}$ 3.4, 5.7, 7.95, 11.9 and 12.85 $\mu$.

NMR Analysis: Signals at $\delta$ 0.08 (singlet, 6 protons, Si(Me)$_2$), 0.88 (singlet, t-butyl), 1.30 (singlet, C-3 methyl), 3.70 (singlet, 3 protons, OCH$_3$), 5.35-5.70 (multiplet, 4 protons, olefinic) ppm.

Mass Spectral Analysis: Calc. M$^+$ + 1 479 m/e: Found M$^+$ + 1 479 m/e. Calc. M$^+$-CH$_3$ 463.3248 m/e: Found M$^+$-CH$_3$ 463.3248 m/e.

EXAMPLE 10 dl-7-(2$\beta$-[(3RS)-3-Hydroxy-3-Methyl-Trans-1-Octenyl]-5-Oxo-1$\alpha$-Cyclopentyl)-Cis-5-Heptenoic Acid, Methyl Ester A solution of 1.0 g. of dl-7-(2$\beta$-[(3RS)-3-t-butyldimethylsilyloxy-3-methyl-trans-1-octenyl]-5-oxo-1$\alpha$-cyclopentyl)-cis-5-heptenoic acid, methyl ester in 5 ml. of tetrahydrofuran, 15 ml. of acetic acid and 5 ml. of water is kept at 25° for 6 hours. After evaporation of the solvents, the residue is dissolved in ether, washed with water, dried and evaporated. Silica chromatography of the residue with 20% ethyl acetate in hexane gives the title product as an oil, 0.492 g.

I. R. Analysis: $\lambda_{max}^{film}$ 2.9, 3.4, 5.65, 6.8, 8.5, 10.1 $\mu$.

NMR Analysis: Signals at $\delta$ 0.88 (triplet, 3 protons, terminal CH$_3$), 1.25 (singlet, C-15 methyl), 1.82 (singlet, OH), 3.65 (singlet, 3 protons, OCH$_3$), 5.38 (multiplet, 2 protons, 5 and 6-H), 5.62 (multiplet, 2 protons 13 and 14-H), ppm.

Mass Spectral Analysis: Calc. M$^+$ 364 m/e: Found M$^+$ 364 m/e. Calc. M$^+$—H$_2$O 346.2507 m/e: Found: M$^+$—H$_2$O 346.2520 m/e.

EXAMPLE 11 dl-7-(2$\beta$-[(3RS)-3-Hydroxy-3-Methyl-Trans-1-Octenyl]-5-Oxo-1$\alpha$-Cyclopentyl)-Cis-5-Heptenoic Acid A solution of 0.40 g. of dl-7-(2$\beta$-[(3RS)-3-hydroxy-3-methyl-trans-1-octenyl]-5-oxo-1$\alpha$-cyclopentyl)-cis-5-heptenoic acid, methyl ester in 25 ml. of tetrahydrofuran and 25 ml. of 0.1N sodium hydroxide is kept at 25° C. for 2.5 hours under nitrogen. The mixture is neutralized with acetic acid and extracted with ether. After washing and drying, the extract is evaporated and the residue chromatographed on silica. Elution with 20% ethyl acetate in hexane gives the title product, as an oil, 0.268 g.

I. R. Analysis: $\lambda_{max}^{film}$ 2.95 (shoulder), 3.4, 5.7, 6.75, 7.0, 8.0, 8.45, 10.05 μ.

NMR Analysis: Signals at δ 0.90 (triplet, 3 protons, terminal CH$_3$), 1.30 (singlet, C-15 methyl), 5.45 (multiplet, 2 protons, 5 and 6-H), 5.65 (multiplet, 2 protons, 13 and 14-H), 6.08 (singlet, 2 protons, OH) ppm.

Mass Spectral Analysis: Calc. M$^+$ —H$_2$O 332.2350 m/e: Found M$^+$ —H$_2$O 332.2313 m/e.

EXAMPLE 12

(l)-7-[2β-((3S)-3-Ethynyl-3-Hydroxy-Trans-1-Octenyl)-5-Oxo-1α-Cyclopentyl]-Cis-5-Heptenoic Acid Treat a solution of 154 mg. of dl-7-[2β-((3S)-3-ethynyl)-3-hydroxy-trans-1-octenyl)-5-oxo-1α-cyclopentyl]-cis-5-heptenoic acid in 5 ml. of acetone with 168 mg. of brucine and concentrate the solution to 2 ml. by heating for 10 minutes. Treat the hot solution with 2 ml. of hexane, seed with a few crystals of the brucine salt of (l)-7-[2β-((3S)-3-ethynyl-3-hydroxy-trans-1-octenyl)-5-oxo-1α-cyclopentyl]-cis-5-heptenoic acid and keep at −10° C. for 7 days. Filter the 122 mg. of crystalline brucine salt and dissolve it by shaking with 30 ml. of water, 0.1 ml. of acetic acid and 20 ml. of ether. Separate the aqueous layer and extract it twice more with ether. Wash the combined ether extracts with water, dry over sodium sulfate and evaporate the solvent. Chromatograph the residue on silica with 20% ethyl acetate in hexane to obtain 31 mg. of the title product as an oil which exhibits $[\alpha]_D^{25}$ = (−) 57° (1% in chloroform) and an NMR spectrum identical to that of the title product prepared from Plexaura homomalla.

EXAMPLE 13

7-(5-Oxo-1-Cyclopentyl)Heptanoic Acid, Methyl Ester

A solution of 8.8 g. of 7-(5-oxo-1-cyclopentenyl)-cis-5-heptenoic acid, methyl ester and 6.6 g. of tris-(triphenylphosphine) rhodium (I) chloride in 800 ml. of 1:1 benzene-ethanol is hydrogenated at 25° and atmospheric pressure until 1 equivalent of hydrogen was absorbed. The solvents are evaporated and the resulting residue dissolved in 1:1 ethyl acetate-hexane and flushed through a silica column. The crude product is then rechromatographed on silica with 15% ethyl acetate in hexane to obtain 7.2 g. of the title product as an oil.

I. R. Analysis: $\lambda_{max}^{film}$ 3.4, 5.7, 5.85, 6.1, 6.95, 8.35, 9.95 μ.

NMR Analysis: Signals at δ 7.32 (multiplet, 1 proton, olefinic), 3.62 (singlet, 3 protons, OCH$_3$) ppm.

Mass Spectral Analysis: Calc. M$^+$ 224.1412 m/e: Found M$^+$ 224.1379 m/e.

EXAMPLE 14 dl-2β-([(3RS)-3-(Tert-Butyldimethylsilyloxy]-3-Methyl-Trans-1-Octenyl)-5-Oxo-1α-Cyclopentyl Heptanoic Acid, Methyl Ester A solution of 7.7 g. of dl-1-iodo-3-tert-butyldimethylsilyloxy-3-methyl-1-octene in 80 ml. of ether is cooled in a dry ice-acetone bath under nitrogen and treated with 32 ml. of 1.24M tert-butyl lithium in pentane. After stirring at −80° for 2 hours, a freshly prepared solution of 6.55 g. of hexamethylphosphorus triamide and 2.6 g. of pentynyl copper in 100 ml. of ether is added to the reaction mixture and stirring continued at −78° under nitrogen for 1 hour. A solution of 4.44 g. of 5-oxo-1-cyclopentenylheptanoic acid, methyl ester in 30 ml. of ether is then added and the mixture stirred at −80° for 1 hour and at 25° for 1 hour under nitrogen. The reaction mixture is added to saturated ammonium chloride solution, extracted with ether and the extract washed with 2% sulfuric acid, filtered through Celite, washed with dilute sodium bicarbonate, water and dried over sodium sulfate. Evaporation and silica chromatography of the residue with 5% ethyl acetate in hexane affords 3.30 g. of the title product as an oil.

I. R. Analysis: $\lambda_{max}^{film}$ 3.4, 5.65, 6.75, 7.9, 8.55, 9.35, 10.15, 11.9, 12.85 μ.

EXAMPLE 15 dl-2β-[(3RS)-3-Hydroxy-3-Methyl-Trans-1-Octenyl]-5-Oxo-1α-Cycloheptane Heptanoic Acid A solution of 3.3 g. of dl-2β-[(3RS)-3-(tert-butyldimethylsilyloxy)-3-methyl-trans-1-octenyl]-5-oxo-1α-cyclopentylheptanoic acid, methyl ester in 15 ml. of tetrahydrofuran, 45 ml. of acetic acid and 15 ml. of water is kept at 25° C for 16 hours under nitrogen. Evaporation of the solvents gives the methyl ester of the title product as an oil. A solution of this crude ester in 150 ml. of tetrahydrofuran and 150 ml. of 0.1 N sodium hydroxide is stirred at 25° under nitrogen for 4 hours, concentrated under vacuum, acidified with acetic acid and extracted with ether. The extract is washed with water, dried over sodium sulfate and evaporated. The resulting residue is chromatographed on silica with 15% ethyl acetate in hexane to obtain 2.025 g. of the title product as an oil.

I. R. Analysis: $\lambda_{max}^{film}$ 3.0, 3.45, 5.75, 5.85, 6.75, 7.8, 8.2, 8.6, 8.9, 10.2 μ.

NMR Analysis: Signals at δ 6.2 (multiplet, 2 protons, OH), 5.65 (multiplet, 2 protons, 13 and 14-H), 1.3 (singlet, 15-CH$_3$) ppm.

EXAMPLE 16

(l)-2β-[(3S)-3-Hydroxy-3-Methyl-Trans-1-Octenyl]-5-Oxo-1α-Cyclopentane Heptanoic Acid A solution of 1.732 g. of dl-2β-[(3RS)-3-hydroxy-3-methyl-trans-1-octenyl]-5-oxo-1α-cyclopentane heptanoic acid in 5 ml. of hot ethyl acetate is diluted with 25 ml. of hot hexane, seeded with a few crystals of the title compound and kept at −10° for 2 days. The resulting crystals are filtered and recrystallized twice as above to obtain 0.50 g. of dl-2β-[(3S)-3-hydroxy-3-methyl-trans-1-octenyl]-5-oxo-1α-cyclopentane heptanoic acid as white crystals, m.p. 95°–97°.

I. R. Analysis: $\lambda_{max}^{KBr}$ 3.0, 3.5, 5.7, 5.85, 7.8, 8.15, 8.9, 10.2 μ.

A solution of 448 mg. of the above crystals in 10 ml. of acetone is treated with 501 mg. of brucine and the solution concentrated to 5 ml. by heating for 5 minutes. The solution is then diluted with 10 ml. of hexane, filtered, seeded with the brucine salt of the title compound and kept at −10° for 6 days. The resulting crystals (205 mg.) are filtered and dissolved by shaking with 15 ml. of water, 0.1 ml. of acetic acid and 15 ml. of ether. The aqueous phase is separated and extracted twice more with ether. The combined ether extracts are washed with water, dried over sodium sulfate and evaporated. The resulting residue is chromatographed on silica with ethyl acetate-hexane mixtures and recrystallized from ethyl acetate-hexane to obtain 67 mg. of the title product as white crystals, m.p. 110°–112°, $[\alpha]_D^{25}$ = (−) 51° (1% in chloroform).

I. R. Analysis: $\lambda_{max}^{KBr}$ 3.0, 3.5, 5.7, 5.85, 7.8, 8.15, 8.25, 8.9, 9.1, 10.2 μ.

EXAMPLE 17

Anesthetized (Dial-urethane) guinea pigs were artificially respired at a constant positive air pressure (Starling miniature pump) and changes in tidal air during inspiration were recorded, according to the method of Rosenthale et al., Int. Arch. Pharmacol., 172, 91 (1968). The bronchoconstrictor agent acetylchlorine (ACH) was administered at doses of 10 to 40 meg/kg. depending on each animal's sensitivity to this compound, and control responses to acetylchlorine were thus established. Bronconstructor agents raise the resistance of the lungs to inflation thereby decreasing the tidal air flow. 7-(2β-[(3S)-3-ethynyl-3-hydroxy-trans-1-octenyl]-5-oxo-1α-cyclopentyl)-cis-5-heptenoic acid was then administered by aerosol, and the animals were then challenged again with acetylcholine, and the degree of inhibition of bronchoconstriction was thus determined. A minimum of two animals was used at each dose.

| | Results[a] |
|---|---|
| Total Aerosol Dose (meg) | Mean % Protection VS ACH Bronchoconstriction |
| $1.5 \times 10^{-4}$ | 32 |
| $10^{-3}$ | 53 |
| $10^{-2}$ | 79 |
| $10^{-1}$ | 92 |

[a]Minimum of 2 animals per dose.

EXAMPLE 18 dl-7-(2β-[(3RS)-3-Trimethylsilylethynyl-3-Trimethylsilyoxy-Trans-1-Octenyl]-5-Oxo-1α-Cyclopentyl)-5-Heptynoic Acid, Methyl Ester A solution of 6.6 g. of dl-1-iodo-3-trimethylsilylethynyl-3-trimethylsilyloxy-1-octene in 30 ml. of ether under nitrogen is cooled in dry ice-acetone bath and treated with 26 ml. of 1.24 M t-butyl lithium in pentane. After stirring at −78° for 2 hours, a freshly prepared solution of 5.08 g. of hexamethyl phosphorus triamide and 2.03 g. of n-propylethynyl copper in 20 ml. of ether is added to the reaction mixture and stirring continued for one hour under nitrogen at −78°. A solution of 3.0 g. of 7-(5-oxo-1-cyclopentyl)-5-heptynoic acid, methyl ester in 15 ml. of ether is then added and the mixture stirred at −78° for 0.5 hour and at 0° for one hour. The reaction mixture is added to saturated ammonium sulfate solution, extracted with ether and the extract washed with 2% sulfuric acid, filtered through Celite, washed with dilute sodium bicarbonate, water and dried. Evaporation and silica chromatography of the residue affords 1.28 g. of the title product as an oil.

I. R. Analysis: $\lambda_{max}^{film}$ 3.4, 4.6, 5.7, 7.98, 11.85 and 13.14 μ. NMR Analysis: δ 0.20 (singlet, 18 protons, Si(Me)$_3$), 0.92 (triplet, 3protons, C-20 methyl), 3.72 (singlet, 3 protons, COOMe), 5.72 (multiplet, 2 protons, olefinic) ppm. Mass Spectral Analysis: MH+ at m/e 517 (theory 517).

EXAMPLE 19 dl-7-(2β-[(3R)-3-Hydroxy-3-Trimethylsilylethynyl-Trans-1-Octenyl]-5-Oxo-1α-Cyclopentyl)-5-Heptynoic Acid, Methyl Ester and dl-7-(2β-[(3S)-3-Hydroxy-3-Trimethylsilylethynyl-Trans-1-Octenyl]-5-Oxo-1α-Cyclopentyl)-5-Heptynoic Acid, Methyl Ester A solution of 1.2 g. of dl-7-(2β-[(3RS)-3-trimethylsilylethynyl-3-trimethylsilyloxy-trans-1-octenyl]-5-oxo-1α-cyclopentyl)-5-heptynoic acid, methyl ester in 6 ml. of acetic acid and 2 ml. of water is stirred at 25° under nitrogen for ¾ hour. The solvent is evaporated at 25° in vacuo and the residue chromatographed on silica gel. Elution with 15% ethyl acetate in hexanes affords 0.30 g. of the first title product as an oil.

I. R. Analysis: $\lambda_{max}^{film}$ 2.9, 3.4, 4.6, 5.7, 7.94, 10.25, 11.5, 11.8, 13.05 and 14.25 μ.

NRM Analysis: Signal at δ 0.2 (singlet, 9 protons, Si(Me)$_3$), 0.9 (triplet, 3 protons, C-20 methyl), 2.42 (singlet, OH), 3.2 singlet, 3 protons, COOMe), 5.66 (doublet, J=15 cps, 1 proton, 14-H), 6.03 (pair of doublets, JJ=7, 15 cps. 1 proton, 13-H) ppm.

Mass Spectral Analysis: MH+ at m/e 445 (theory 445).

Continuing elution with 15% ethyl acetate in hexanes yields 0.29 g. of the second title product as an oil.

I. R. Analysis: $\lambda_{max}^{film}$ 2.9, 3.4, 4.6, 5.7, 7.95, 10.25, 11.5, 11.8, 13.05 and 14.25 μ.

NMR Analysis: Signals at δ 0.18 (singlet, 9 protons, Si(Me)$_3$), 0.9 (triplet, 3 protons, C-20 methyl), 2.42 (singlet, OH) 3.68 (singlet, 3 protons, COOMe), 5.73 (doublet, J=15 cps, 14-H), 6.02 (pair of doublets, JJ=6.5, 15 cps, 13-H) ppm.

Mass Spectral Analysis: MH+ at m/e 445 (theory 445).

EXAMPLE 20 dl-7-(2β-[(3R)-3-Ethynyl-3-Hydroxy-Trans-1-Octenyl]-5-Oxo-1α-Cyclopentyl)-5-Heptynoic Acid A solution of 0.28 g. of dl-7-(2β-[(3R)-3-hydroxy-3-trimethylsilylethynyl-trans-1-octenyl]-5-oxo-1α-cyclopentyl)-5-heptynoic acid, methyl ester in 6 ml. of tetrahydrofuran and 6 ml. of 1N sodium hydroxide solution is stirred at 25° for 20 hours under nitrogen. The mixture is acidified with acetic acid, diluted with ether, washed with brine and dried with magnesium sulfate. The solvent is evaporated and the residue chromatographed on silica gel. Elution with 20% ethyl acetate in hexanes affords 0.2 g. of the title product as an oil.

I. R. Analysis: $\lambda_{max}^{film}$ 3.1, 3.45, 5.8, (shoulder), 10.3 μ.

NMR Analysis: Signals at δ 0.9 (triplet, 3 protons, C-20 methyl), 2.60 (singlet, C≡CH), 5.59 (singlet, 2protons, OH), 5.72 (doublet, J=15 cps, 14-H), 6.15 (pair of doublets, JJ=7.5, 15 cps, 13-H) ppm.

Mass Spectral Analysis: M+-C$_5$H$_{11}$ at m/e 287 (theory 287).

EXAMPLE 21 dl-7-(2β-[(3S)-3-Ethynyl-3-Hydroxy-Trans-1-Octenyl]-5-Oxo-1α-Cyclopentyl)-5-Heptynoic Acid A solution of 0.27 g. of dl-7-(2β-[(3S)-3-hydroxyl-3-trimethylsilylethynyl-trans-1-octenyl]-5-oxo-1α-cyclopentyl)-5-heptynoic acid, methyl ester in 6 ml. of tetrahydrofuran and 6 ml. of 1N sodium hydroxide solution is stirred at 25° for 20 hours under nitrogen. The mixture is acidified with acetic acid, diluted with ether, washed with brine and dried with magnesium sulfate. The solvent is evaporated and the residue chromatographed on silica gel. Elution with 20% ethyl acetate in hexanes affords 0.21 g. of the title product as an oil.

I. R. Analysis: $\lambda_{max}^{film}$ 3.1, 3.4, 5.75, 5.85 (shoulder), 10.3μ.

NMR Analysis: Signals at δ 0.9 (triplet, 3 protosn, C-20 methyl), 2.62 (singlet, C CH), 5.63 (doublet, J=14 cps, 13-H), 6.05 (pair of doublets, JJ=7.5, 14 cps. 13-H) ppm.

Mass Spectral Analysis: M+ at m/e 358 (theory 358).

EXAMPLE 22 dl-7-(2β-[(3RS)-3-(t-Butyldimethylsilyloxy)-3-Methyl-Trans-1-Octenyl]-5-Oxo-1α-Cyclopentyl)-5-Heptynoic Acid, Methyl Ester A solution of 6.0 g. of dl-1-iodo-3-(t-butyldimethylsilyloxy-3-methyl-1-octene in 30 ml. of ether under nitrogen is cooled in a dry ice-acetone bath and treated with 26 ml. of 1.24 M t-butyl lithium in pentane. After stirring at −78° for 2 hours, a freshly prepared solution of 5.08 g. of hexamethylphosphorus triamide and 2.03 g. of n-propylethynyl copper in 20 ml. of ether is added to the reaction mixture and stirring continued for one hour under nitrogen at −78°. A solution of 3.08 g. of 7-(5-oxo-1-cyclopentenyl)-5-pentynoic acid, methyl ester in 15 ml. of ether is then added and the mixture stirred at −78° for 0.5 hour and at 0° for one hour. The reaction mixture is added to saturated ammonium sulfate solution, extracted with ether and the extract washed with 2% sulfuric acid, filtered through Celite, washed with diluted sodium bicarbonate, water and dried. Evaporation and silica chromatography the residue affords 3.9 g. of the title product as an oil.

I. R. Analysis: $\lambda_{max}^{film}$ 3.4, 5.7, 8.0, 11.95, 12.4, 12.9 μ.

NMR Analysis: Signals at δ 0.09 (singlet, 6 protons, Si(Me)₂), 0.86 (singlet, 9 protons, t-butyl), 1.28 (singlet, 15-methyl), 3.67 (singlet, 3 protons, COOCH₃), 5.62 (multiplet, 2 protons, olefinic), ppm.

Mass Spectral Analysis: MH+ at m/e 477 (theory 477).

EXAMPLE 23 dl-7-(2β-[(3RS)-3-Hydroxy-3-Methyl-Trans-1-Octenyl]-5-Oxo-1α-Cyclopentyl)-5-Heptynoic Acid, Methyl Ester A solution of 3.8 g. of dl-7-(2β-[(3RS)-3-(t-butyldimethylsilyloxy)-3-methyl-trans-1-octenyl]-5-oxo-1α-cyclopentyl)-5-heptynoic acid, methyl ester in 10 ml. of tetrahydrofuran, 30 ml. of acetic acid and 10 ml. of water is kept at 25° for 4½ hours. After evaporation of the solvent, the residue is dissolved in ether, washed with water, dried and evaporated. Silica gel chromatography of the residue with 16% ethyl acetate in hexanes gives 1.6 g. of the title product as an oil.

I. R. Analysis: $\lambda_{max}^{film}$ 2.9, 3.4, 8.62 and 10.3 μ.

NMR Analysis: Signals at δ 0.9 (triplet, 3 protons, C-20 methyl), 1.30 (singlet, C-15 methyl), 2.08 (singlet, OH), 3.7 (singlet, 3 protons, COOMe), 5.70 (multiplet, 2 protons, olefinic) ppm.

Mass Spectral Analysis: M+—H₂O at m/e 344 (theory 344).

EXAMPLE 24 dl-7-(2β-[(3RS)-3-Hydroxy-3-Methyl-Trans-1-Octenyl]-5-Oxo-1α-Cyclopentyl)-5-Heptynoic Acid A solution of 1.5 g. of dl-7-(2β-[(3RS)-3-hydroxy-3-methyl-trans-1-octenyl]-5-oxo-1α-cyclopentyl)-5-heptynoic acid, methyl ester in 12 ml. of tetrahydrofuran and 12 ml. of 0.1 N sodium hydroxide solution is stirred at 25° for 4½° hours under nitrogen. The mixture is acidified with acetic acid, diluted with ether, washed with water and dried. The solvent is evaporated and the residue chromatographed on silica gel. Elution with 20% ethyl acetate in hexanes affords 0.95 g. of the title product as an oil.

I. R. Analysis: $\lambda_{max}^{film}$ 3.0 (shoulder), 3.4, 5.72, 8.6 and 10.25 μ.

NMR Analysis: signals at δ 0.89 (triplet, 3 protons, C-20 methyl), 1.30 (singlet, C-15 methyl), 5.73 (multiplet, 2 protons, olefinic), 6.28 (singlet, 2 protons, OH) ppm.

Mass Spectral Analysis: M+—H₂O at m/e 332 (theory 332).

EXAMPLE 25

Following the procedure of Example 17, but substituting dl-7-(2β-[(3R)-3-ethynyl-3-hydroxy-trans-1-octenyl]-5-oxo-1α-cyclopentyl)-5-heptynoic acid as the compound administered, the following results are obtained:

| Total aerosol dose (meg.) | Mean % Protection vs. ACH Bronchoconstriction |
| --- | --- |
| 1.5 × 10⁻² | 12 |
| 1.5 × 10⁻¹ | 33 |
| 1.5 × 10⁰ | 32 |
| 1.5 × 10 | 23 |

EXAMPLE 26

Following the procedure of Example 17, but substituting dl-7-(2β-[(3S)-3-ethynyl-3-hydroxy-trans-1-octenyl]-5-oxo-1α-cyclopentyl)-5-heptynoic acid as the compound administered, the following results are obtained:

| Total aerosol dose (meg.) | Mean % Protection vs. ACH Bronchoconstriction |
| --- | --- |
| 1.5 × 10⁻³ | 0 |
| 1.5 × 10⁻² | 29 |
| 1.5 × 10⁻¹ | 47 |
| 1.5 × 10⁰ | 98 |

EXAMPLE 27

Following the procedure of Example 17, but substituting dl-7-(2β-[(3RS)-3-hydroxy-3-methyl-trans-1-octenyl]-5-oxo-1α-cyclopentyl)-5-heptynoic acid as the compound administered, the following results are obtained:

| Total aerosol dose (meg.) | Mean % Protection vs. ACH Bronchoconstriction |
| --- | --- |
| 1.5 × 10⁻¹ | 0, 56 (2 tests) |
| 1.5 × 10⁰ | 27, 29 (2 tests) |
| 1.5 × 10 | 45 |

EXAMPLE 28

Male Charles River rats weighing between 200–300 g. are deprived of food but not water for 24 hours prior to use. Water is, however, withheld during the experiment. The rats are weighed, anesthetized with ether, and the pylorus ligated according to the method of Shay et al., Gastroenterology, 26, pp. 906–913 (1954). Treatment or vehicle control is then administered subcutaneously. Rats are housed 2/cage and sacrificed with $CO_2$ four hours after ligation. The stomachs are removed, rinsed, and the contents emptied into a graduated centrifuge tube. The tubes are centrifuged for 20 minutes at 20,000 R.P.M. and the volume of gastric juice recorded. Any samples obviously contaminated by feces, food, or hemolysis are eliminated. An aliquot of each is frozen for later determination of $Na^+$, $K^+$ and $Cl^-$ concentration. The pH is measured and 1 ml. of gastric juice is titrated with 0.1 N NaOH to a pH of 7.0–7.4. The data are analyzed by either a student's t-test or an analysis of variance depending upon which test is appropriate.

| Compound and Dose | Results<br>Findings and Comments |
|---|---|
| dl-7-(2β-[(3R)-3-ethynyl-3-hydroxy-trans-1-octenyl]-5-oxo-1α-cyclopentyl)-5-heptynoic acid 4 mg./kg. | no weight change, statistically significant decrease in volume. increase in pH, increase in $Na^+$ meq/liter, no change $K^+$ meq/liter, no change $Cl^-$ meq/liter, statistical sign decrease in vol/100 g., decrease in $H^+$ meq/liter, decrease in total secreted meq/liter. Comment: Interesting activity |
| dl-7-(2β-[(3S)-3-ethynyl-3-hydroxy-trans-1-octenyl]-5-oxo-1α-cyclopentyl)-5-heptynoic acid 4 mg./kg. | no weight change, statistically significant decrease in volume, increase in pH, increase in $Na^+$ meq/liter, no change in $K^+$ meq/liter, no change $Cl^-$ meq/liter, statistical significant decrease in vol/100 g., no change in $H^+$ meq/liter, decrease in total secreted meq/liter. Comment: Interesting activity |

The subject matter which the applicants regard as their invention is particularly pointed out and distinctly claimed as follows:

1. A compound of the formula:

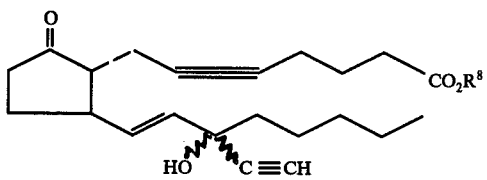

wherein $R^8$ is hydrogen, alkyl of from 1 to about 6 carbon atoms, alkali metal, or a pharmacologically acceptable cation derived from ammonia or a basic amine.

2. A compound as defined in claim 1 which is dl-7-(2β-[(3R)-3-ethynyl-3-hydroxy-trans-1-octenyl]-5-oxo-1α-cyclopentyl)-5-heptynoic acid.

3. A compound as defined in claim 1 which is dl-7-(2β-[(3S)-3-ethynyl-3-hydroxy-trans-1-octenyl]-5-oxo-1α-cyclopentyl)-5-heptynoic acid.

* * * * *